United States Patent
Setty

(10) Patent No.: US 10,835,123 B2
(45) Date of Patent: *Nov. 17, 2020

(54) VIRTUAL REALITY IMAGING OF THE BRAIN

(71) Applicant: Gateway Institute for Brain Research, LLC, Fort Lauderdale, FL (US)

(72) Inventor: Yaakov Setty, Ramat Gam (IL)

(73) Assignee: Gateway Institute for Brain Research, LLC, Fort Lauderdale, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/573,117

(22) Filed: Sep. 17, 2019

(65) Prior Publication Data

US 2020/0008679 A1 Jan. 9, 2020

Related U.S. Application Data

(63) Continuation of application No. 15/896,344, filed on Feb. 14, 2018, now Pat. No. 10,456,042.

(51) Int. Cl.
*G06K 9/00* (2006.01)
*A61B 5/00* (2006.01)
(Continued)

(52) U.S. Cl.
CPC .......... *A61B 5/0042* (2013.01); *A61B 5/055* (2013.01); *A61B 5/4064* (2013.01);
(Continued)

(58) Field of Classification Search
CPC ................................................ G06T 2210/41
See application file for complete search history.

(56) References Cited

U.S. PATENT DOCUMENTS

| 2014/0058189 A1* | 2/2014 | Stubbeman | A61N 2/006 600/13 |
| 2014/0153690 A1* | 6/2014 | Claus | A61B 6/025 378/9 |

(Continued)

OTHER PUBLICATIONS

Collins et al (NPL: "Design and Construction of a Realistic Digital Brain Phantom", IEEE Transactions on Medical Imaging, vol. 17, No. 3, Jun. 1998, p. 6.) (Year: 1998).*

(Continued)

*Primary Examiner* — Oneal R Mistry
(74) *Attorney, Agent, or Firm* — Christopher & Weisberg, P.A.

(57) ABSTRACT

A method for imaging the brain of a living patient includes creating and displaying an unconstrained 3D virtual reality image of the brain of the living patient based on a plurality of 3D images captured by magnetic resonance imaging (MRI). An administration of a drug is simulated into brain tissue. The simulation includes displaying a simulated diffusion of the drug in 3D VR image of the brain; displaying simulated brain tissue uptake of the drug in the 3D VR image of the brain; displaying a simulated stimulation of individual neurons in the 3D VR image of the brain; and analyzing a simulated activity of the individual neurons based on at least one predetermined property of the drug. The method further includes determining a brain treatment protocol based at least in part on the simulated administration of the drug into the brain.

20 Claims, 15 Drawing Sheets

(51) Int. Cl.
  *G06T 15/10*    (2011.01)
  *H04N 13/261*   (2018.01)
  *A61B 5/055*    (2006.01)
  *G16H 20/10*    (2018.01)
  *G16H 50/50*    (2018.01)

(52) U.S. Cl.
  CPC ............ *A61B 5/7275* (2013.01); *G06T 15/10* (2013.01); *G16H 20/10* (2018.01); *H04N 13/261* (2018.05); *A61B 2576/026* (2013.01); *G16H 50/50* (2018.01)

(56) References Cited

U.S. PATENT DOCUMENTS

| | | | | |
|---|---|---|---|---|
| 2014/0330195 | A1* | 11/2014 | Peterson | A61K 31/4439 604/20 |
| 2017/0061034 | A1* | 3/2017 | Ritchey | A61B 5/4064 |
| 2019/0105105 | A1* | 4/2019 | Zagorchev | A61B 5/0042 |

OTHER PUBLICATIONS

Taswell. "BrainWatch Software for Interactive Exploration of Brain Scans in 3D Virtual Reality System" IEEE, 2017 (Year: 2017).*
Adamovich. "A virtual reality-based system integrated with FMRI to study neural mechanism of action observation execution: A proof of concept study" Restorative Neurology and Neuroscience 27 (2009) DOI 10.3233/RNN-2009-0471. 2009 (Year: 2009).*

* cited by examiner

Axial                    Coronal

Sagittal                 Unconstrained

VIRTUAL REALITY IMAGING OF THE BRAIN

CROSS-REFERENCE TO RELATED APPLICATION

This application is a continuation of U.S. patent application Ser. No. 15/896,344, filed on Feb. 14, 2018 entitled "VIRTUAL REALITY IMAGING OF THE BRAIN," the entirety of which is incorporated herein by reference.

STATEMENT REGARDING FEDERALLY SPONSORED RESEARCH OR DEVELOPMENT n/a

TECHNICAL FIELD

The present invention relates to a method and system for imaging the brain, and in particular, using virtual reality to simulate intranasal drug delivery to the brain.

BACKGROUND

The brain acts as the center of the nervous system and is among the most complex and uncharacterized systems of the human body. It is composed of billions of neurons that control numerous complex processes directing the course of maintaining normal body function Neurodegenerative diseases such as Alzheimer and Parkinson's disease are severe disorders with acute symptoms that gradually progresses over time until death. The complexity of the brain and its related disorders requires arduous study, thus mechanisms underlying brain functionality remain poorly understood and effective disease-modifying treatments for neurodegenerative disorders are yet to be developed. Moreover, understanding the progression of neurodegenerative disorders is currently difficult to follow in the brain of a living organism and most of the data is collected by imaging (MRI, PET, SPECT) at a specific time point or by post mortem pathology. This makes it difficult to track the underlying mechanisms dictating the dynamics of the degeneration process, as well as to examine the effectiveness of treatment strategies. Consequently, drug development for neurodegenerative diseases is a rather slow and challenging process and treatments are often determined by repetitive trial and error cycles.

SUMMARY

The present invention advantageously provides a method for imaging the brain of a living patient. The method includes creating and displaying an unconstrained three-dimensional virtual reality image of the brain of the living patient based on a plurality of three-dimensional images captured by magnetic resonance imaging (MRI). An administration of a drug is simulated into brain tissue of the living patient. The simulation includes displaying a simulated diffusion of the drug in three-dimensional virtual reality image of the brain of the living patient; displaying simulated brain tissue uptake of the drug in the three-dimensional virtual reality image of the brain of the living patient; displaying a simulated stimulation of individual neurons in the three-dimensional virtual reality image of the brain of the living patient; and analyzing a simulated activity of the individual neurons based on at least one predetermined property of the drug. The method further includes determining a brain treatment protocol based at least in part on the simulated administration of the drug into the brain of the living patient.

In another aspect of this embodiment, the three-dimensional virtual reality image of the brain is created and displayed in real-time.

In another aspect of this embodiment, the simulated administration of the drug into the brain is intranasal.

In another aspect of this embodiment, the simulated administration of the drug is provided by a virtual reality machine having a virtual reality headset.

In another aspect of this embodiment, the brain tissue is the substantia nigra.

In another aspect of this embodiment, displaying the simulated diffusion of the drug further includes identifying a nasal passage on the three-dimensional image of the brain and simulating the diffusion of the drug beginning at the image of the nasal passage.

In another aspect of this embodiment, displaying the simulated diffusion of the drug further includes simulating the diffusion of the drug at a plurality of doses at a plurality of time durations, and displaying the simulated diffusion of the drug at each of the plurality of doses and each of the plurality of time durations.

In another aspect of this embodiment, displaying the simulated diffusion of the drug includes: assigning a plurality of voxels to the brain tissue in the three-dimensional virtual reality image of the brain of the living patient; determining a diffusion coefficient between adjacent ones of the plurality of voxels based in part on an MRI intensity in each of the plurality of voxels; determining a concentration of the drug in each of the plurality of voxels based in part on the diffusion coefficient between adjacent ones of the plurality of voxels; and displaying the simulated diffusion of the drug in real time.

In another aspect of this embodiment, displaying the simulated brain tissue uptake of the drug includes: assigning a plurality of voxels to the brain tissue in the three-dimensional virtual reality image of the brain of the living patient; determining an absorption coefficient for each of plurality of voxels based in part on an MRI intensity in each of the plurality of voxels; determining a tissue uptake of the drug in each of the plurality of voxels based in part on the absorption coefficient in each of the plurality of voxels; and displaying the simulated brain tissue uptake of the drug in real time.

In another aspect of this embodiment, displaying a simulated stimulation of individual neurons includes: assigning a plurality of voxels to the brain tissue in the three-dimensional virtual reality image of the brain of the living patient, each voxel being associated with at least one individual neuron; uniformly assigning a plurality of simulated reactive agents within an area of the image occupied by the substantia nigra in the three-dimensional virtual reality image of the brain of the living patient, each of the plurality of simulated reactive agents being configured to respond to a predetermined environmental condition; and if one of the plurality of simulated reactive agents responds to the predetermined environmental condition, providing a visual indication of the response in an associated one of the plurality of voxels in real time.

In another aspect of this embodiment, analyzing a simulated activity of the individual neurons based on at least one predetermined property of the drug includes characterizing the simulated activity of the individual neurons at a predetermined dose of the drug as at least one from the group consisting of: unstimulated; stimulated and partially activated; and stimulated and fully activated.

In another aspect of this embodiment, determining a brain treatment protocol based at least in part on the simulated administration of the drug into the brain of the living patient includes determining an initial dosing of the drug.

In another embodiment, a system for imaging the brain includes a control unit having a processor, the processor having processing circuitry configured to create and display an unconstrained three-dimensional virtual reality image of the brain of the living patient based on a plurality of three-dimensional images captured by magnetic resonance imaging (MRI); simulate an administration of a drug into brain tissue of the living patient, the processing circuitry being further configured to: display a simulated diffusion of the drug in the three-dimensional virtual reality image of the brain of the living patient; display simulated brain tissue uptake of the drug in the three-dimensional virtual reality image of the brain of the living patient; display a simulated stimulation of individual neurons in the three-dimensional virtual reality image of the brain of the living patient; and analyze a simulated activity of the individual neurons based on at least one predetermined property of the drug; and determine a brain treatment protocol based at least in part on the simulated administration of the drug into the brain of the living patient.

In another aspect of this embodiment, displaying the simulated diffusion of the drug further includes simulating the diffusion of the drug at a plurality of doses at a plurality of time durations, and displaying the simulated diffusion of the drug at each of the plurality of doses and each of the plurality of time durations.

In another aspect of this embodiment, displaying the simulated diffusion of the drug includes: assigning a plurality of voxels to the brain tissue in the three-dimensional virtual reality image of the brain of the living patient; determining a diffusion coefficient between adjacent ones of the plurality of voxels based in part on an MRI intensity in each of the plurality of voxels; determining a concentration of the drug in each of the plurality of voxels based in part on the diffusion coefficient between adjacent ones of the plurality of voxels; and displaying the simulated diffusion of the drug in real time.

In another aspect of this embodiment, displaying simulated brain tissue uptake of the drug includes: assigning a plurality of voxels to the brain tissue in the three-dimensional virtual reality image of the brain of the living patient; determining an absorption coefficient for each of plurality of voxels based in part on an MRI intensity in each of the plurality of voxels; determining a tissue uptake of the drug in each of the plurality of voxels based in part on the absorption coefficient in each of the plurality of voxels; and displaying the simulated brain tissue uptake of the drug in real time.

In another aspect of this embodiment, displaying a simulated stimulation of individual neurons includes: assigning a plurality of voxels to the brain tissue in the three-dimensional virtual reality image of the brain of the living patient, each voxel being associated with at least one individual neuron; uniformly assigning a plurality of simulated reactive agents within an area of the image occupied by the substantia nigra in the three-dimensional virtual reality image of the brain of the living patient, each of the plurality of simulated reactive agents being configured to respond to a predetermined environmental condition; and if one of the plurality of simulated reactive agents responds to the predetermined environmental condition, providing a visual indication of the response in an associated one of the plurality of voxels in real time.

In another aspect of this embodiment, analyzing a simulated activity of the individual neurons based on at least one predetermined property of the drug includes characterizing the simulated activity of the individual neurons at a predetermined dose of the drug as at least one from the group consisting of: unstimulated; stimulated and partially activated; and stimulated and fully activated.

In another aspect of this embodiment, the processing circuitry is configured to create and display in real-time.

In another embodiment, a method of imaging a brain of a living patient includes capturing a plurality of three-dimensional images of the brain of the living patient with magnetic resonance imaging (MRI). An unconstrained three-dimensional virtual reality image of the brain of the living patient is created and displayed based on the plurality of three-dimensional images in real-time. An intranasal administration of a drug into brain tissue of the living patient is simulated in real-time. The simulation includes: displaying a simulated diffusion of the drug in three-dimensional virtual reality image of the brain of the living patient; displaying simulated brain tissue uptake of the drug in the three-dimensional virtual reality image of the brain of the living patient; displaying a simulated stimulation of individual neurons in the substantia nigra three-dimensional virtual reality image of the brain of the living patient; and analyzing a simulated activity of the individual neurons based on at least one predetermined property of the drug. A drug dosing is determined based at least in part on the simulated administration of the drug into the brain of the living patient.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1:
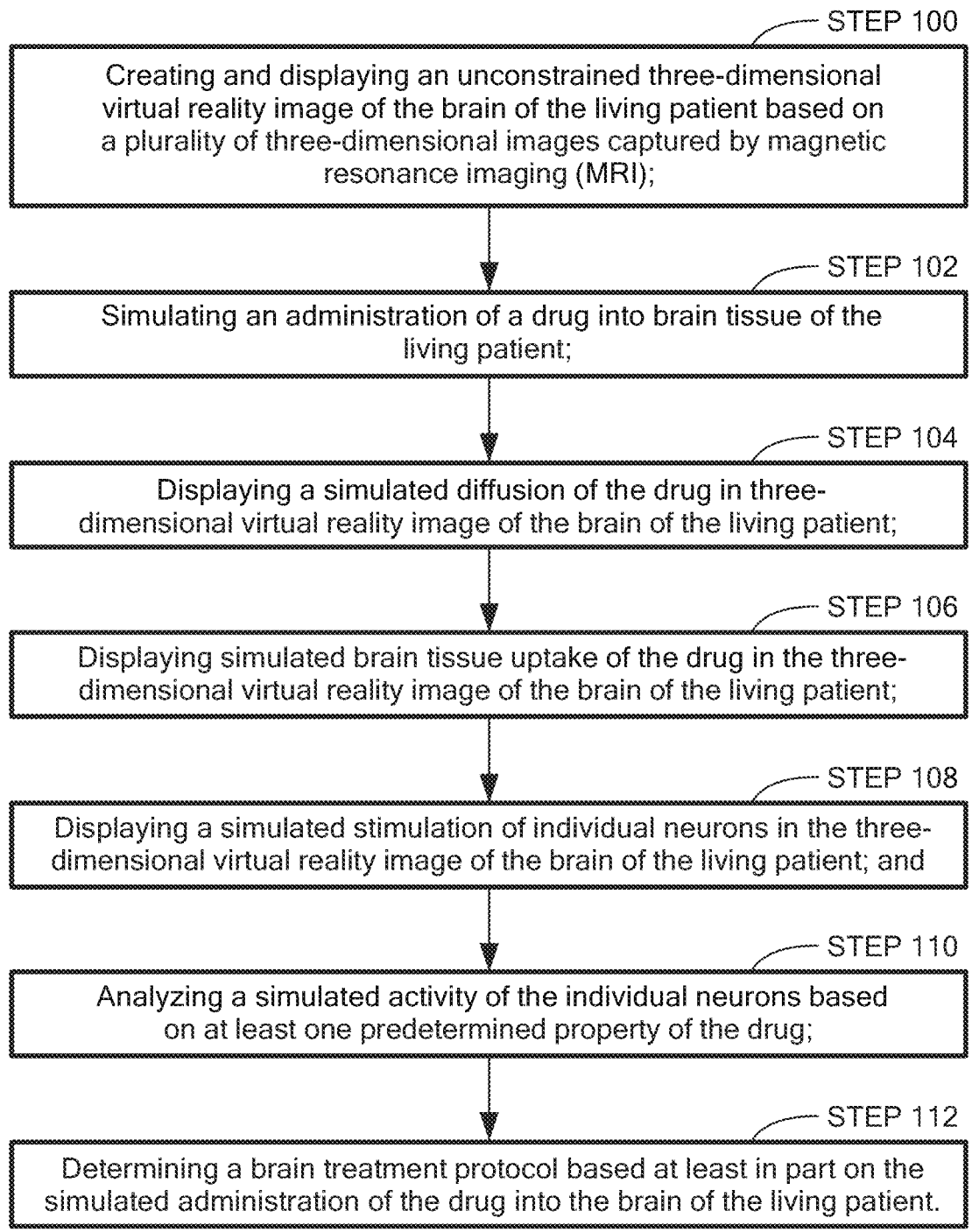
FIG. 1 is a flow chart illustrating a method of imaging a brain of a living patient in accordance with the principles of the present application.

Referring now to the drawings in which like reference designators refer to like elements, there is show in FIG. 1 an exemplary method of using virtual reality to image the brain of a living patient, whether human or animal, for use during a simulated drug delivery to the brain. The method includes creating and displaying an unconstrained three-dimensional (3D) virtual reality image of the brain of the living patient based on a plurality of three-dimensional images captured by magnetic resonance imaging (MRI) (Step 100). In an exemplary configuration, a human patient is placed in an MRI machine and the MRI is split into individual slice images. The sliced images are placed in virtual three-dimensional space according to their originally captured positions (see FIG. 2). The virtual space spanned by the MRI may then be divided into a three-dimensional grid containing a plurality of voxels, for example, approximately 500,000 grid voxels (matrix of 257×80×24), each including a set of properties representing the state of neural tissue and a volumetric factor concentration at its location. At intervals of set time-steps, the simulation runs a series of calculations in order to update the properties for each of the plurality of voxels. Cellular agents are designed as autonomous entities that are able to sense their close vicinity and can act independently to determine their next step. An additional grid maintains the coordinates and pointers for these agents.

To display a 3D internal view of the MRI while allowing changes during the course of the simulation, a material renderer, for example, Unreal Engine's material renderer, interprets the virtual images to create a specialized computer code and wraps them around 3D objects to draw representations of those objects on the computer display as a set of localized colored pixels. Textures may be blended and deformed as a function of 3D location, light incidence angles, and other factors. A 3D representation of the MRI data is generated by building a custom volumetric material and each MRI slice sub-image is assigned to a corresponding position in 3D space. When the volumetric material is applied to a 3D object, for every point on the object, the colors of the MRI slices are linearly interpolated on either side of that point in the virtual space and the resulting color for the rendered pixel is displayed, for example, with an Oculus or other virtual reality (VR) interactive device or machine having a headset.

Figure 2:
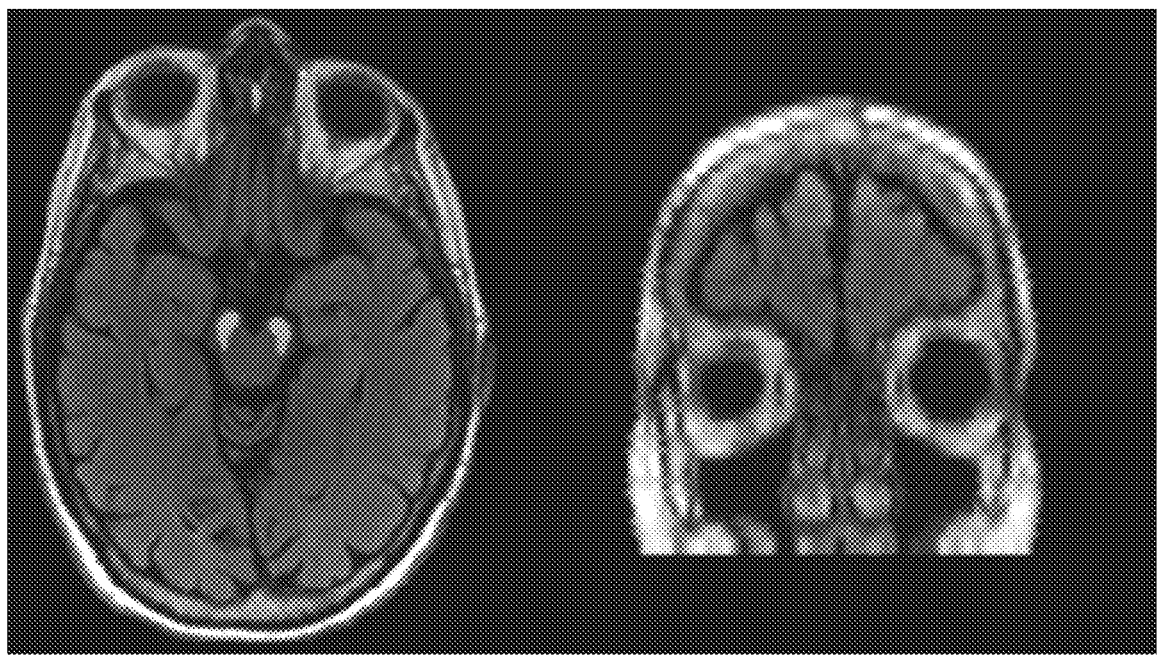
FIG. 2 is an illustration of a brain MRI showing axial, coronal, and sagittal planes of the brain and an unconstrained view of an approximately 45 degree plane from a forehead of the patient.
Figure 2:
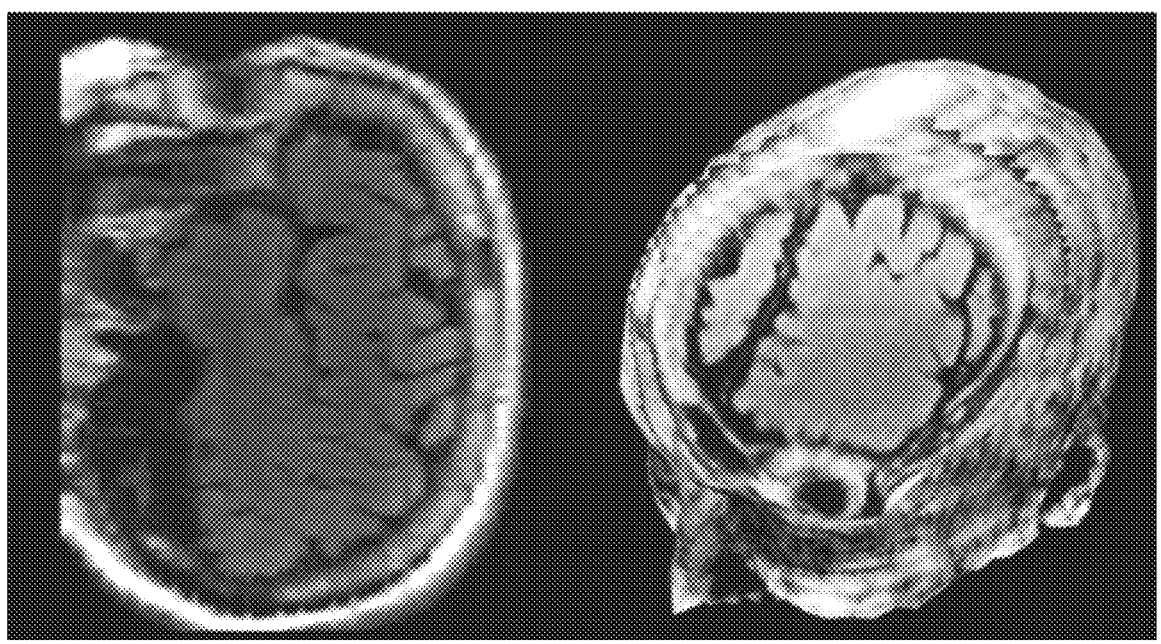
Figure 3A:
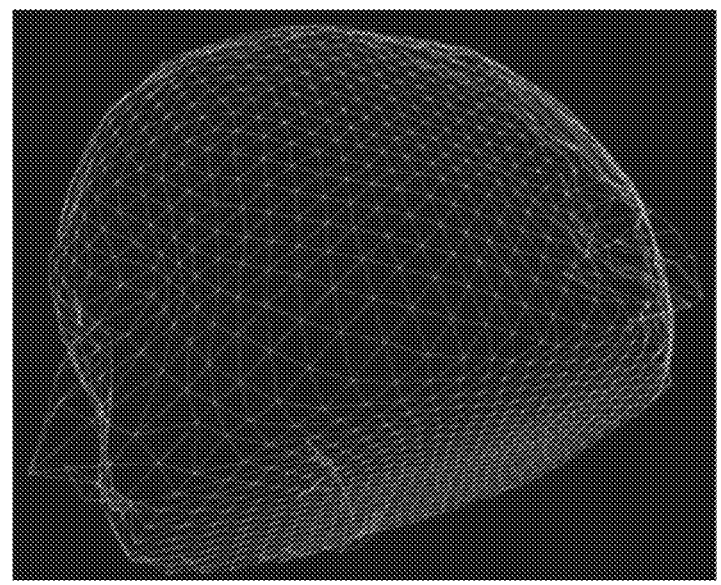
FIG. 3A is an image of an exemplary external surface mesh generated from the brain MRI used for the 3D visualization in accordance with the method shown in FIG. 1.

The volumetric material is applied to two separate 3D objects for both external and internal views of the MRI. For external views of the skull, a 3D surface is generated that encloses all points in 3D space that are contained within the volumetric material, and the volumetric material is further used render the MRI at all points on this 3D surface. An exemplary external surface mesh generated by the MRI used in the simulation is shown in FIG. 3A. For internal views of the MRI, a virtual screen is created in a 3D plane located in front of the VR camera and moves simultaneously with it. The volumetric material is applied to this virtual screen such that the portion of the MRI located a set distance in front of the camera is visible. The volume material is processed in real-time, therefore additional data can be layered on top of the MRI. As shown in FIG. 2, a completely unconstrained view of the MRI data, viewable from any angle, at any zoom level, and from any position, is created. Areas of interest (e.g., nose, substantia nigra) are superimposed. This allows for the creation of dynamically select multiple layers of 3D data for comprehensive visualization.

Figure 3B:
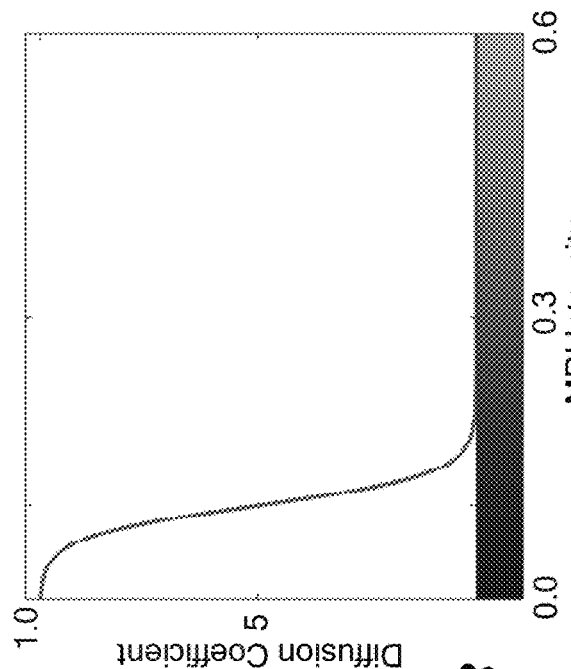
FIG. 3B is a graph showing an exemplary solution for a diffusion equation as fraction of MRI intensity from black to white.
Figure 3C:
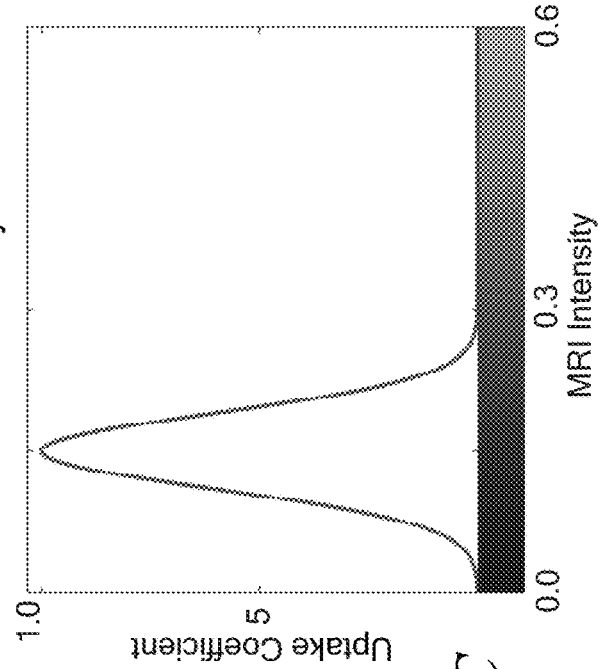
FIG. 3C is a graph showing an exemplary solution for a tissue uptake equation as function of MRI intensity from black to white.
Figure 3D:
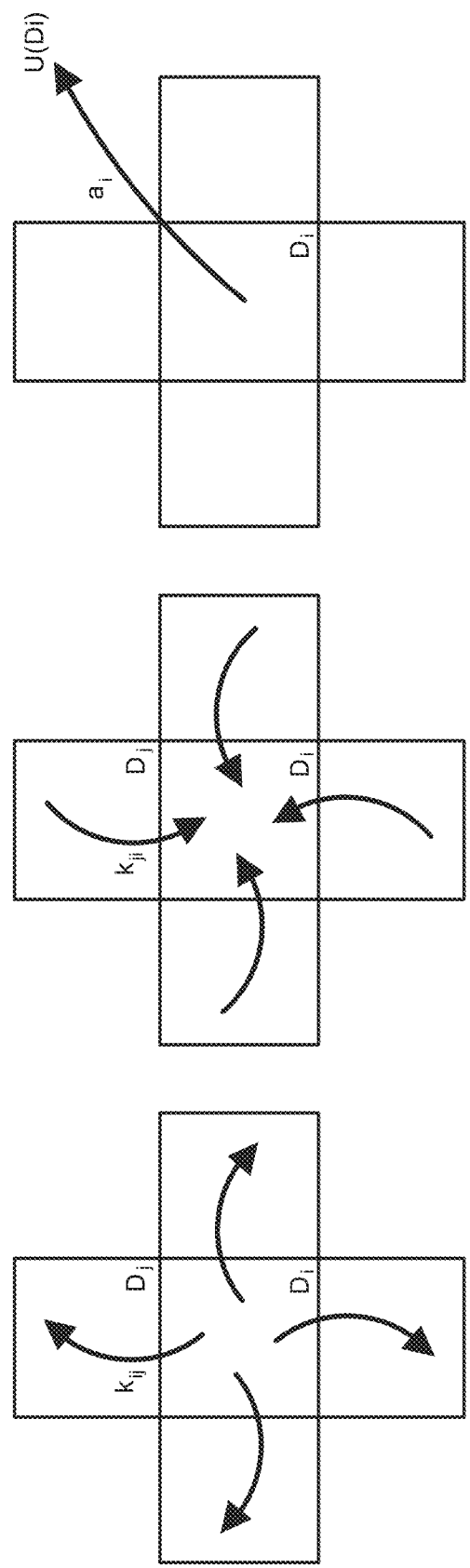
FIG. 3D is an illustration of drug diffusion and absorption in an exemplary three-dimensional grid overlying the MRI data captured using the method shown in FIG. 1.

The method further includes simulating an administration of a drug into brain tissue of the living patient (Step 102). In an exemplary method, the simulated administration of the drug into the brain tissue occurs intranasaly, although it is contemplated that any modality for drug administration into the brain may be imaged by the disclosed method, for example, intravenous, intragastric, and intrathecal delivery system. The simulation further includes displaying a simulated diffusion of the drug in the 3D VR image of the brain of the living patient (Step 104). To simulate intranasal drug delivery, for example, a delivery location within the nasal cavity is marked on the MRI designating the plurality of voxels corresponding to that location. These designated voxels are set as the origin for calculating the diffusion of the set quantity of drug to be delivered. For diffusion simulation, a diffusion of the drug through the brain is assumed to be driven by tissue density. In regions with the highest density where the MRI intensity is lightest (e.g., bones) diffusion is assumed to be minimal. In regions with the lowest density, where the MRI intensity is darkest (e.g., liquid areas, cerebrospinal fluid) diffusion is assumed to be at a maximum. For gray areas, it is assumed a diffusion coefficient (k) varies with shade from minimal to maximum values. The diffusion coefficient is calculated as a function of MRI intensity in each of the plurality of voxels according to a reverse logistic function with midpoint=0.1 and steepness=60 (FIG. 3B). Discretization of a master equation (1) is used to simulate drug diffusion between adjacent one of the plurality of voxels where "D" is the drug concentration, "k" is the diffusion coefficient between adjacent ones of the plurality of voxels, and "U(D)" is the tissue uptake (see equation (2) below). For each time-step, the simulation sums the fraction of the drug that is delivered from neighboring voxels and subtracts the fraction that is delivered to the adjacent cells (FIG. 3D). The diffusion rate between two adjacent ones of the plurality of voxels is determined based on their MRI intensity color.

$$D_i^{n+1} = D_i^n - \Delta t \sum_j k_{ij} D_i^n + \Delta t \sum_j k_{ji} D_j^n - U_i^n(D_i) \quad (1)$$

Figure 4:
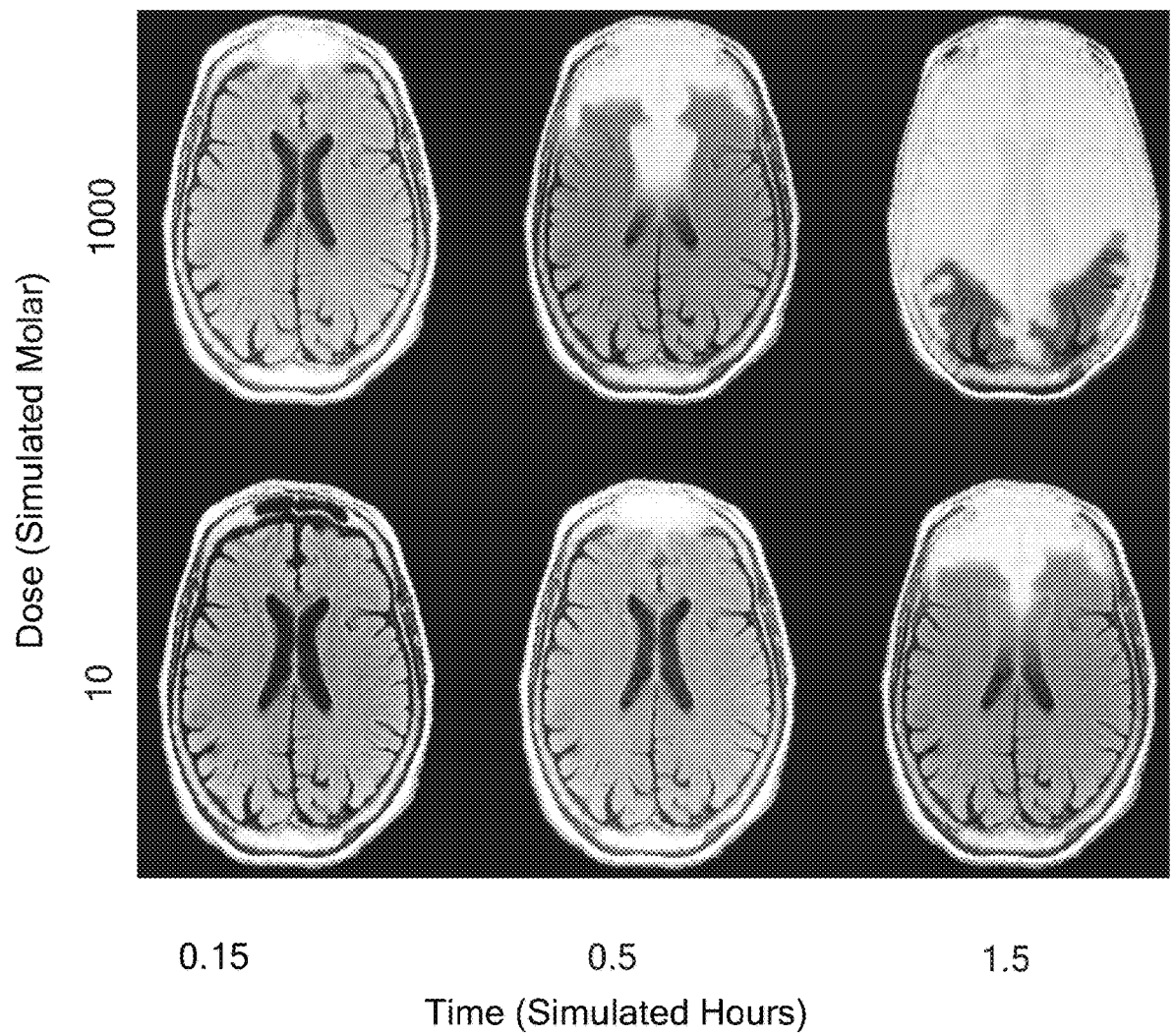
FIG. 4 is an illustration of a simulated drug diffusion in a slice of a brain MRI over the axial plane. The lighter areas denote drug concentration and sampling points are at time 0.15, 0.5, 1.5 simulated hours under 10e3 and 1000e3 simulated Molar dose.

Drug concentrations are visualized in real-time as varying intensities of, for example, an orange highlight overlaid on the 3D VR image. The simulation and visualization are in continuous communication, such that the highlight intensity is updated on the display as the simulation progresses. This allows for the monitoring of simulated intranasal factor flow through the simulation in real-time. An example drug diffusion in a slice of a brain MRI over the axial plane is shown in FIG. 4.

Simulated brain tissue uptake of the drug is further displayed in the 3D VR image of the brain of the living patient (Step 106). To calculate tissue uptake (i.e., the manner in which the drug is compounded to increase tissue ability to absorb the drug), an absorption coefficient and saturation concentration threshold are defined for each of the plurality of voxels. MRI intensity is used as indication of as tissue density to derive the uptake parameters for the calculation. Accordingly, a correlation between tissue density and its ability to absorb the simulated drug is assumed. Therefore, higher uptake in gray areas (i.e., brain tissue) are set and lower uptake at black and white areas (liquid and bone, respectively) are further set. The absorption capacity is approximated as a specialized Gaussian function (defines the "a" parameter in equation 2 below) of MRI intensity where the maximum value is normalized to 1 (FIG. 3C). The MRI intensity for maximum absorption is calculated as the Gaussian mean ($\mu$) and the range of intensities, where significant absorption occurs is described by the Gaussian standard deviation ($\sigma$), where (a) is the absorption coefficient of the particular voxel of the plurality of voxels (see illustration in FIG. 3D). The default solution with $\mu=0.15$ and $\sigma=0.04$ is given in FIG. 3C. ($\mu$) may be derived from the distribution of MRI colors. Discretization of the tissue uptake function is given in Equation 2 below:

$$U_i^n(D) = a_i D_i^n \quad (2)$$

Figure 5:
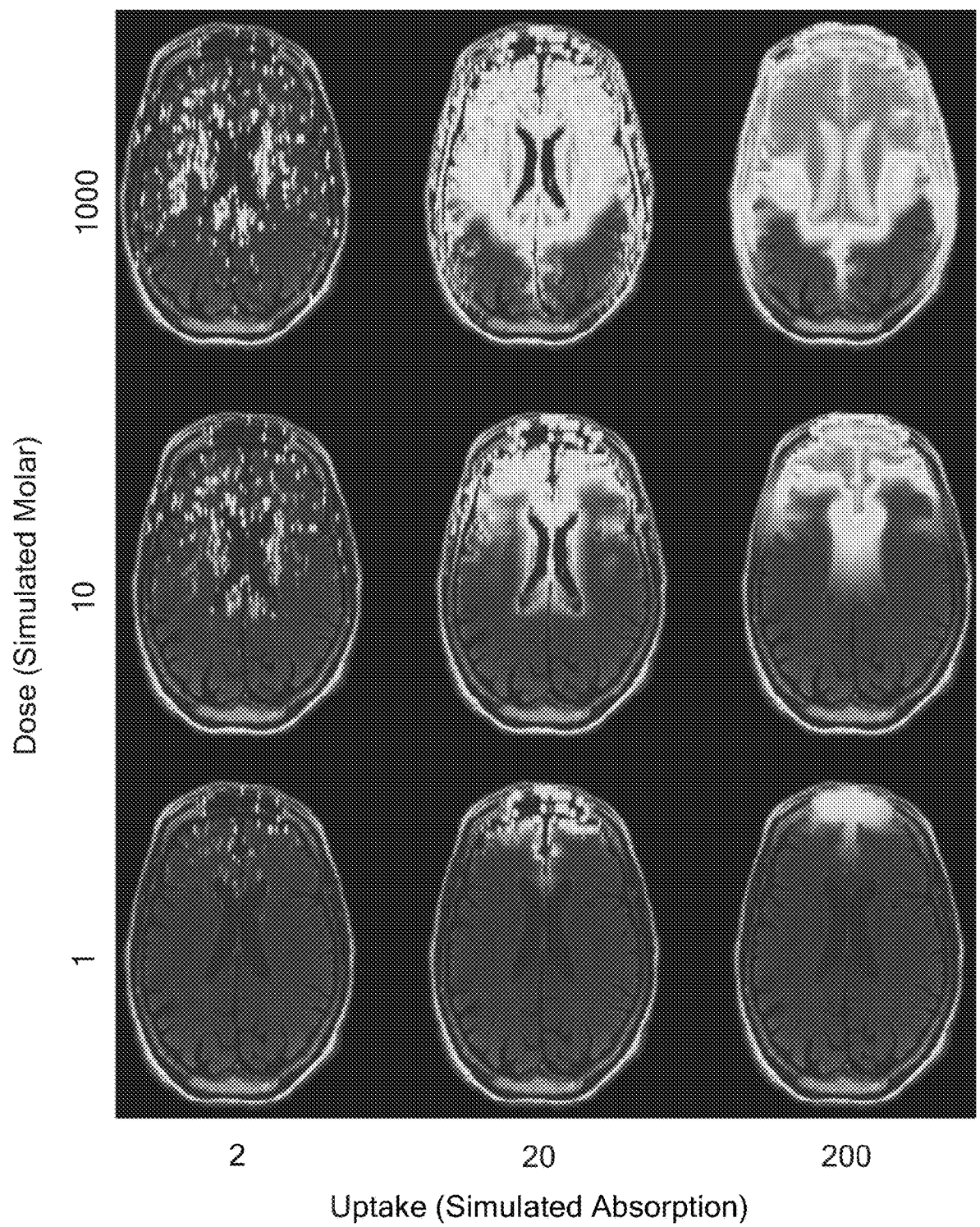
FIG. 5 is an illustration of an exemplary tissue uptake of a slice of brain tissue of over the axial plain under differed uptakes and doses parameters in accordance with the principles of the present application. Uptake levels are colored from low (gray) to high (white). Sampling points at time 1 simulated hour, dose: 1e3, 10e3 and 1000e3 simulated Molar and tissue uptake of 2e-3 20e-3 and 200e-3 simulated absorption units.

The tissue uptake may be visualized in real time by highlighting the 3D MRI reproduction using, for example, Matlab jet scale color bar (from blue to red, or any color range) indicating the current level of absorption saturation at each location. Voxels that have not absorbed any intranasal factor are may be indicated by a predetermined color, for example, blue. An example of tissue uptake of an MRI slice of over an axial plain under differed uptakes and doses parameters is shown in FIG. 5. Uptake levels are displayed from low (gray) to high (white). Sampling points at time 1 simulated hour, dose: 1e3, 10e3 and 1000e3 simulated Molar and tissue uptake of 2e-3 20e-3 and 200e-3 simulated absorption units.

A simulated stimulation of individual neurons in the 3D VR image of the brain of the living patient may further be displayed (Step 108). In one configuration, at the area of the substantia nigra in the 3D VR image, simulated reactive agents are uniformly or randomly positioned to indicate stimulation of the neurons within the virtual space. For example, the locations of where neurons of the substantia nigra region are positioned are marked on the MRI slice images. When the simulation is executed, this position of the neurons is combined with the 3D VR plurality of voxels assignment. At each run, the simulation places the simulated reactive agents randomly in the marked area, creating a uniform distribution of agents in a slightly different pattern at each run. Agents carry a synthetic molecular stimulation mechanism that triggers a response once it senses a predetermined environmental signal or condition. It is further assumed that the stimulation is irreversible and there is no degradation of the intrinsic activity. If one of the simulated reactive agents responds to the predetermined environmental condition, a visual indication of the response is provided in an associated one of the plurality of voxels in real time.

Figure 6:
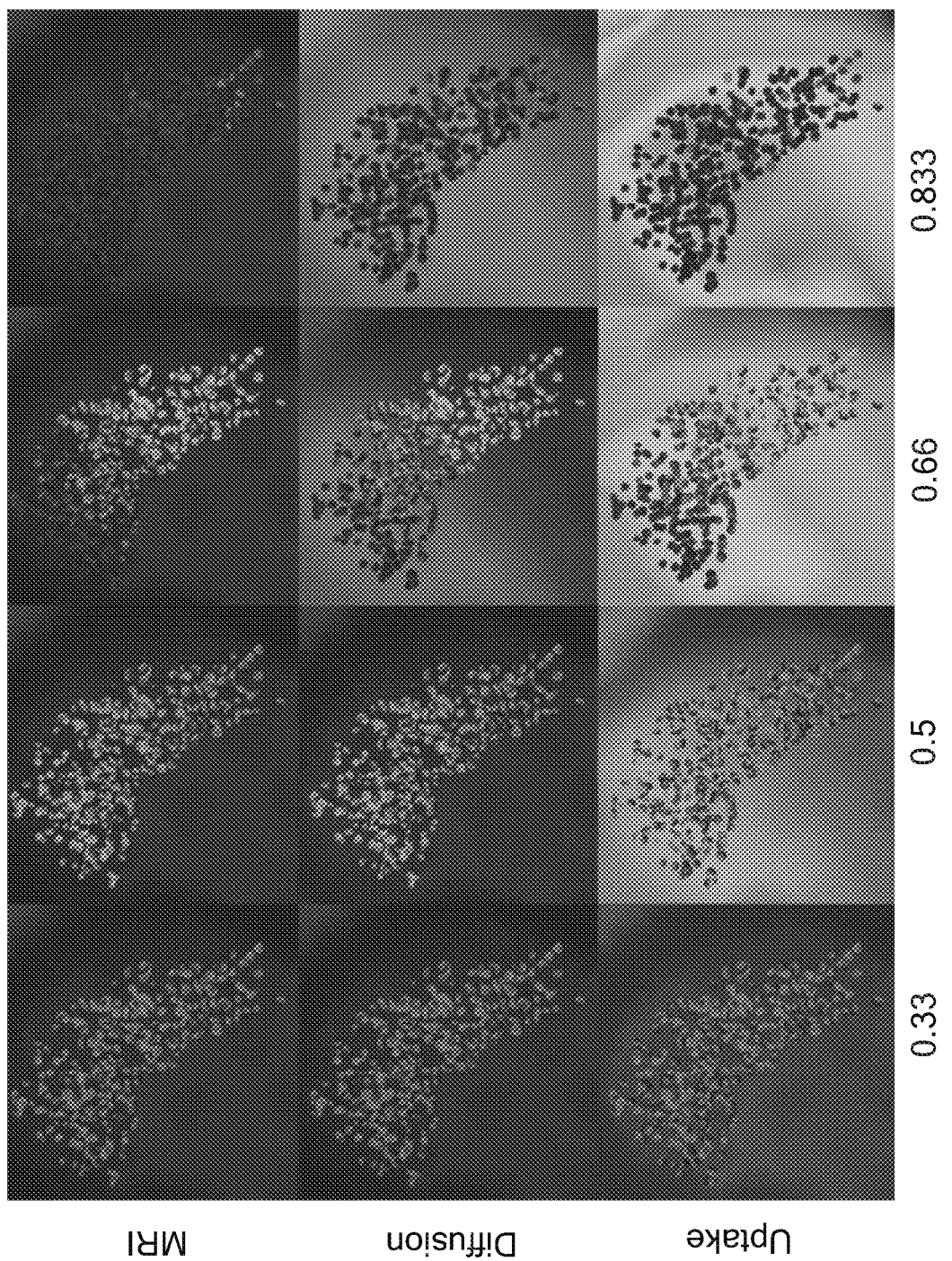
FIG. 6 is an illustration showing cell stimulation over the population in the pars compacta region of the substantia nigra presented in three different modes, MRI (top), diffusion (middle) and tissue uptake (bottom). Four sampling points at time 0.33, 0.5, 0.66 and 0.833 simulated hours under tissue uptake of 40e-3 simulated absorption capacity and dose of 100e3 simulate Molar. Cells in the unstimulated form are colored white, stimulated and partially activated cells change their color to light gray, and to gray when they are stimulated and fully activated.

In one simulation with 1000 neurons (approximately four orders of magnitude less than in an 80 years old patient's substantia nigra) are visualized as sphere-like globules that are colored green and are pulsing radially as an indication of internal metabolic activity. The amplitude of the scale change is adjusted according its internal state. The neurons remain one color, for example, green, as long as they are not stimulated. In one configuration, initial neuron stimulation occurs once the neuron senses drug up-take of at least 0.33% of the maximum capacity of the voxel where it is positioned, although any drug uptake percentage may be set by the method. Once a neuron triggers stimulation it reflects the change by shifting its color from the initial color, to a second color, for example, yellow, and then a third color, for example, red, upon reaching full stimulation. A fully stimulated neuron terminates its pulse. FIG. 6 shows an exemplary neuron stimulation over the population in the pars *compacta* region of the substantia nigra (presented in three different modes, MRI (top), diffusion (middle) and tissue uptake (bottom)). Four sampling points at time 0.33, 0.5, 0.66 and 0.833 simulated hours under tissue uptake of 40e-3 simulated absorption capacity and dose of 100e3 simulate Molar. Neurons in the native form are colored gray, partially stimulated cells change their color to light gray, and to dark white when they are fully stimulated.

Figure 7B:
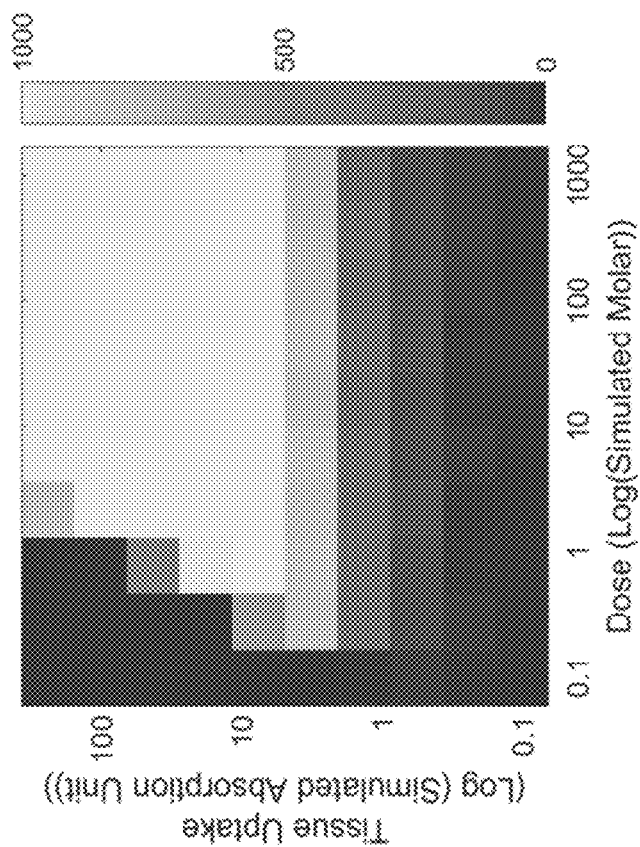
FIG. 7B is a graph showing cell population maximum capacity as a function of dose and tissue uptake.
Figure 7A:
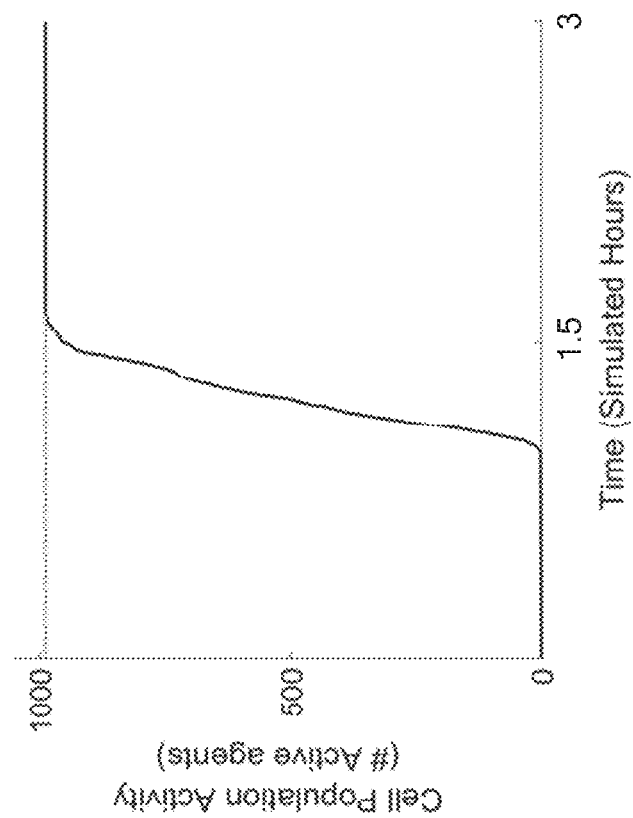
FIG. 7A is a graph showing cell population activity averaged over multiple simulation runs under the same conditions and showing a maximum capacity (dotted line)
Figure 7D:
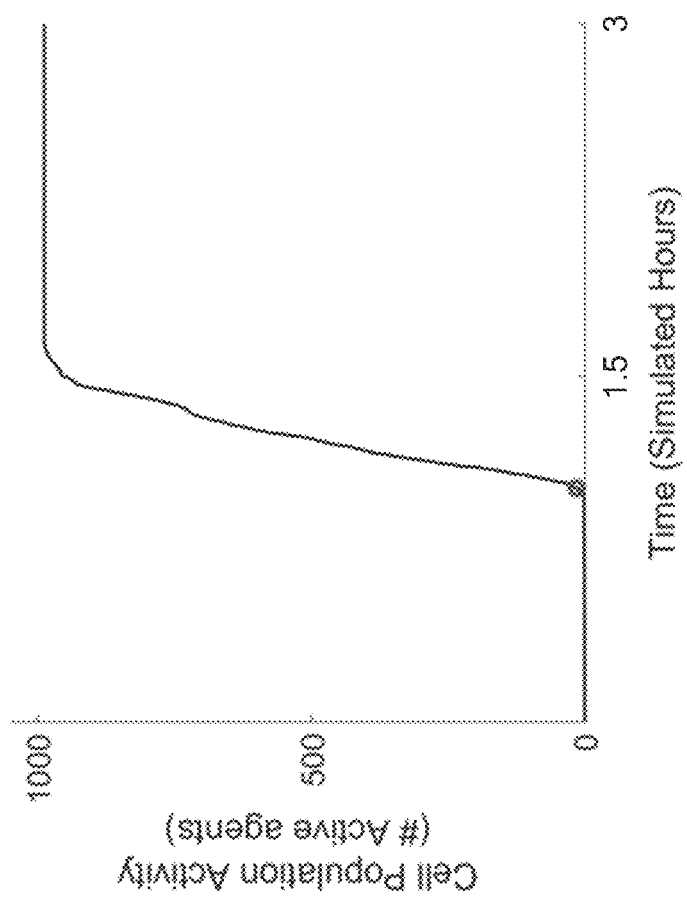
FIG. 7D is a graph showing cell population activity averaged over multiple simulation runs under the same conditions and showing an activity lag (circle)
Figure 7C:
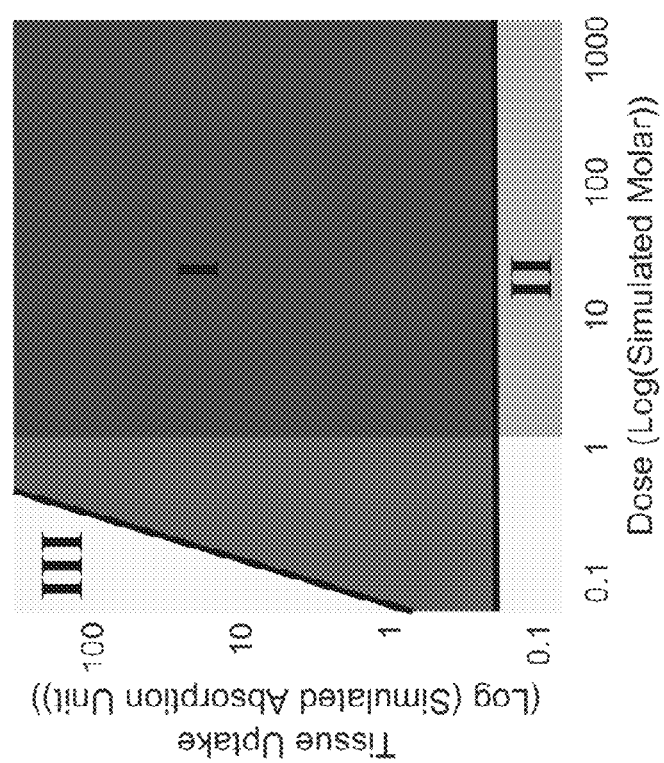
FIG. 7C is a schematic representation of cell population maximum capacity function regimes and activity domains.
Figures 7E, 7F:
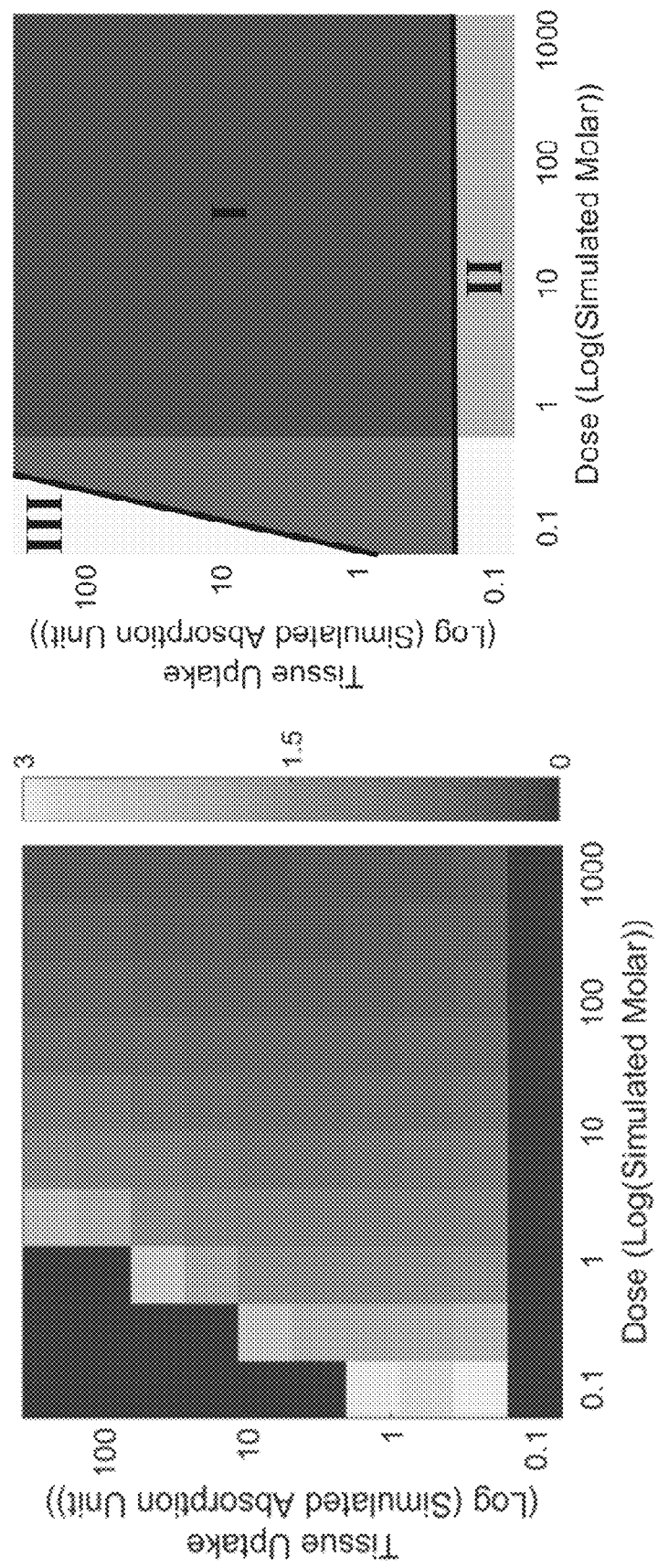
FIG. 7E is a graph showing cell population activity lag as a function of tissue uptake and dose.
FIG. 7F is a schematic representation of cell population activity lag regimes and activity domains.
Figure 7H:
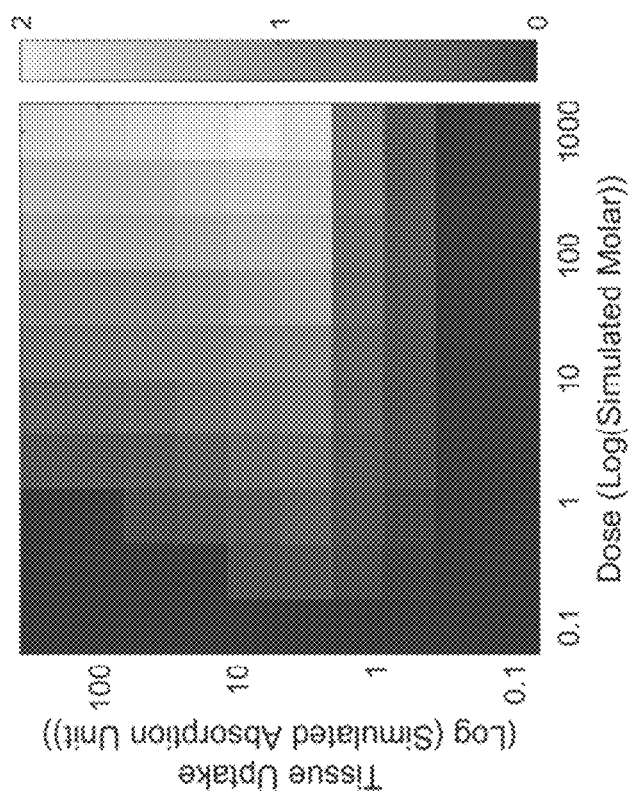
FIG. 7H is a graph showing cell population reaction rate as a function of tissue uptake and dose.
Figure 7G:
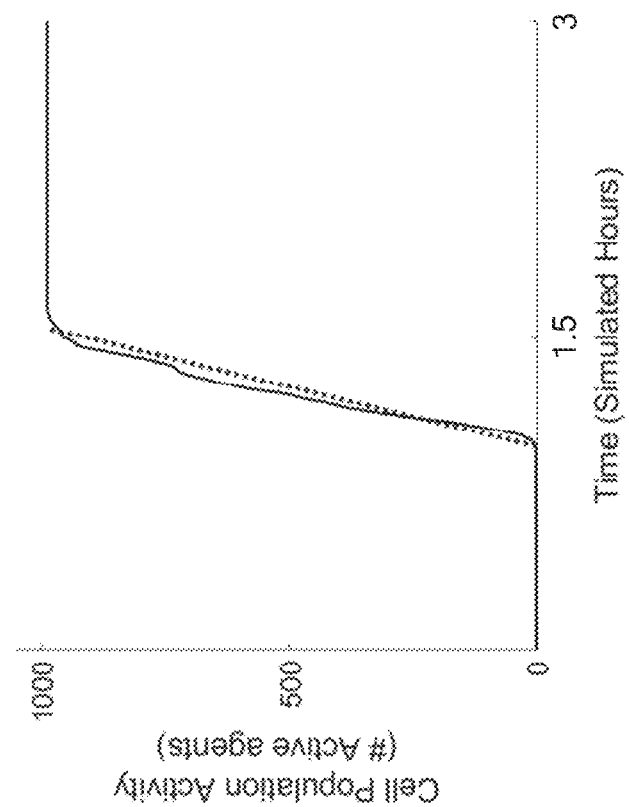
FIG. 7G is a graph showing cell population averaged over multiple simulation runs under the same condition and showing a reaction rate (dotted line)
Figure 7I:
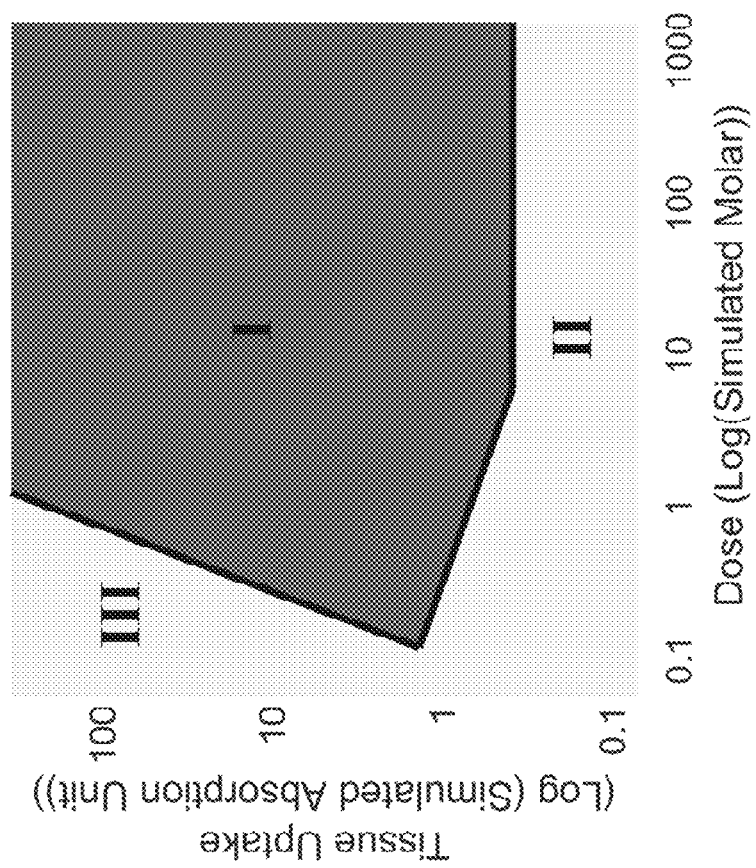
FIG. 7I is a schematic representation of cell population reaction rate regimes and activity domains.

Referring now to FIGS. 7A-7I, a simulated activity of the individual neurons based on at least one predetermined property of the drug is analyzed (Step 110) and a brain treatment protocol based at least in part on the simulated administration of the drug into the brain of the living patient is determined (Step 112). To determine a brain treatment protocol, hidden functions of the simulation extracted from multiple simulation runs are analyzed. FIG. 7A shows maximum capacity (gray dotted line) as calculated in a plot of neuron activity over time. FIG. 7B shows capacity as a function of dose and tissue uptake. FIG. 7C shows a schematic representation of capacity function regimes and activity domains. FIG. 7D shows activity lag (circle) as calculated in a plot of neuron activity over time. FIG. 7E shows activity lag as a function of tissue uptake and dose. FIG. 7F shows a schematic representation of activity lag function regimes and activity domains. FIG. 7G shows a reaction rate (dotted line) as calculated in a plot of neuron activity over time. FIG. 7H shows a reaction rate as a function of tissue uptake and dose. FIG. 7I shows a schematic representation of reaction rate function regimes and activity domain. FIGS. 7A, 7D, and 7G are representative simulations run under dose ~2e3 and uptake ~1e-3. Maps in FIGS. 7B, 7E, and 7H are calculated for 100 runs with different tissue uptakes and dose (dose 100e-3:0.001e-3; uptake 100e-3:0.001e-3). Schematic representations shown in FIGS. 7C, 7F, and 7I are designated monotonic (dark gray), skewed distribution functions (light gray), and the activity domains: I—activation area, II—no activity due to insufficient tissue uptake, III—no activity due to absorption at tissues prior to the substantia nigra.

An analysis of the simulated reactions reveal three hidden functions: maximum capacity (FIG. 7A), activity lag (FIG. 7D), and reaction rate (FIG. 7G). Characterizing the functions includes execution of the simulations under various doses and tissue uptake combinations and plotted in a two dimensional map for each function (See FIGS. 7B, 7E, and 7H). The maps disclose apparent distinct variations between simulations under different initial conditions. The dose and tissue uptake combinations elicit equilibrium for the hidden function, and extending the analyzed range has a minor effect on the results. A monotonic behavior as a function of the dose for all three functions (x-axis in FIGS. 7B, 7E, and 7H) is observed. That is, for a fixed tissue uptake the functions preserve the order and the simulation capacity and reaction rate show non-decreasing order (FIGS. 7B and 7H, respectively) while activity lag shows non-increasing order (FIG. 7E). However, the parameter as a function of tissue uptake did not show a uniform behavior. Maximum capacity and activity lag acts differently in two strict regimes: (1) monotonic regime where the function preserve an order and (2) skewed distribution regime where the function increases to a maximum point and then decreases (y-axis in FIGS. 7B, 7E, and 7H). Maximum capacity (FIG. 7B) and activity lag (FIG. 7E) show non-decreasing monotonic behavior when a specific threshold of dose is crossed (~5e3 and ~1e3 simulated Molar, respectively). The response rate as a function of tissue uptake shows a skewed distribution regime with no monotonic regime (FIG. 7E). The shape and amplitude of the skewed distribution function varied between the doses of each plot. For example, the maximum slope for 1000e3 doses (~2.0 cells/sec) is given approximately at simulated tissue uptake of 10e-3 simulated absorption units and decreases to zero as the uptake decreases to 1.5 cells/sec when reaches 150e-3 simulated absorption units. A schematic description of the different regimes for each hidden function for the tissue uptake values is given in FIGS. 7C, 7F, and 7I where dark gray indicates a monotonic regime and light gray indicates a skewed distribution one. The apparent skewed distribution regimes suggest that there is an optimal tissue uptake value where it most effectively influences the substantia nigra area responsiveness. Decreasing below this value, reduces the ability of the brain tissue to absorb the infused drug, whereas increasing above this value, enhances the uptake of the entire tissue and which leads to drug absorption in the areas prior to the substantia nigra. Moreover, at an intermediate dose at the skewed distribution regimes, we observe that the response area is bounded by an interdependency diagonal threshold. This analysis characterizes three activity domains: I—activation area, where the population is stimulated, II—no activity due to insufficient tissue uptake and III—no activity due to absorption at tissues period to the substantia nigra (FIGS. 7C, 7F, 7I). The interdependency diagonal thresholds (black line) where higher doses compensates for lower uptake, and vice versa, in getting similar output (FIGS. 7C, 7F, 7I). The maximum capacity and activity lag shows a single interdependency diagonal (approximately at 0.1e3-5e3 and 0.1e3-10e3 dose, respectively) whereas the activation rate shows two interdependency diagonals. One at the 0.1e3-1e3 dose range for low tissue up-take (0.1e-3-1e-3 simulated absorption units) and the other at the 0.1e3-10e3 dose range for high tissue uptake (1e-3-100e-3 simulated absorption units).

Figure 8B:
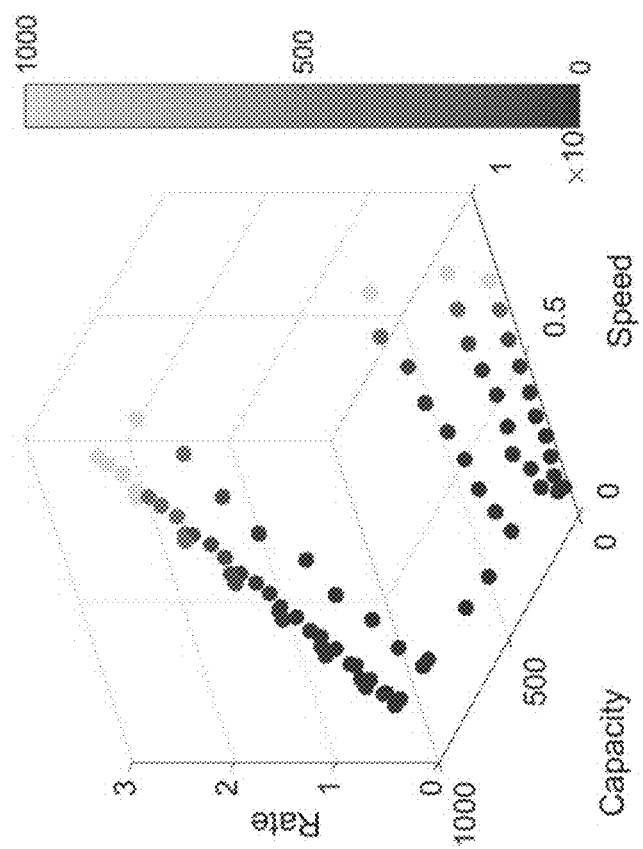
FIG. 8B is a 3D scatter plot of treatment possibilities labeled based on their dose concentration.
Figure 8A:
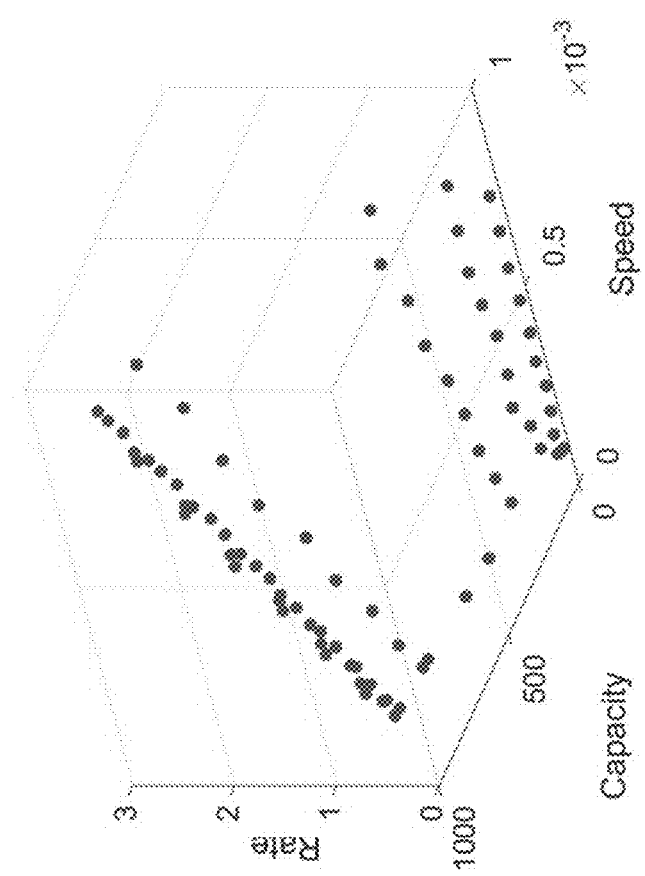
FIG. 8A is a 3D scatter plot of 100 treatment possibilities as a function of rate, speed, and capacity.
Figure 8D:
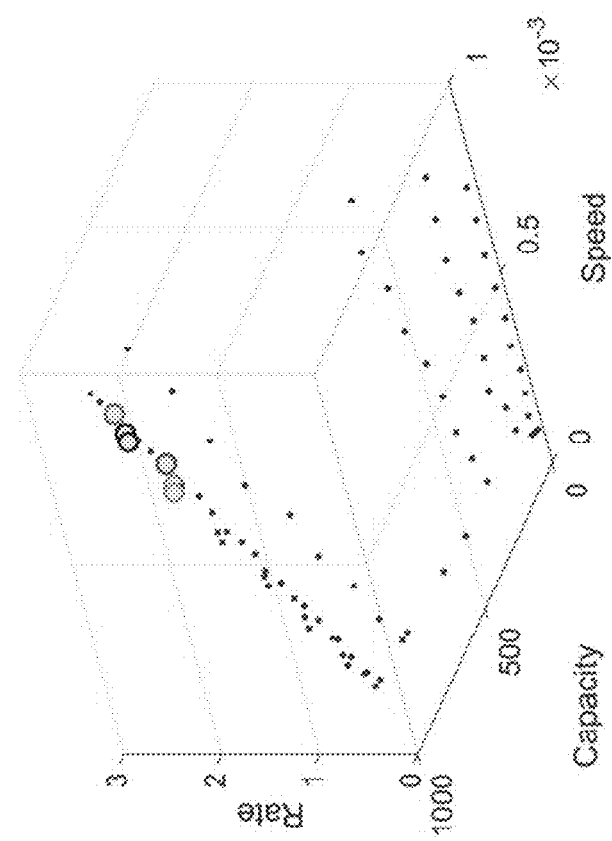
FIG. 8D is a 3D scatter plot showing cost-efficient treatments screened over treatment possibilities.
Figure 8C:
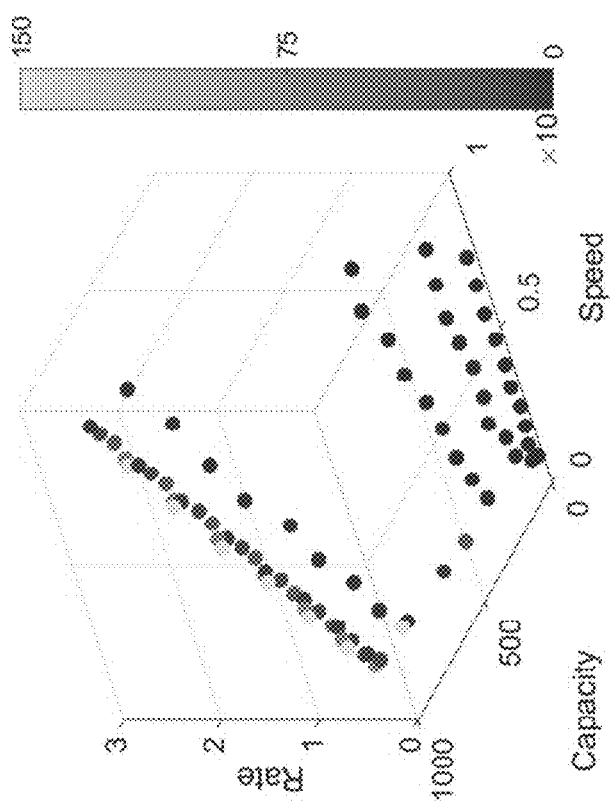
FIG. 8C is a 3D scatter plot of treatment possibilities labeled based on their uptake level.

Referring now to FIGS. 8A-8D, to determine which treatment combinations offer the most cost-effective treatment, the output values of the three hidden functions are calculated in a three-dimensional space whose axis indicates the functions. That is, on the x-axis the speed of reaction (i.e., 1/activity lag) is position, on the y-axis the reaction rate is positioned, and on the z-axis the capacity of the function. Each data point in the plot represents a treatment in the hidden function 3D space (FIG. 8A). The results show two clusters, one at the higher capacity (>700 stimulated cells) and one at the lower capacity (<400 stimulated cells). The minority of the treatment combinations are placed in the intermediate zone. These results correspond with the hidden function analysis reveal a steep incline from the base value to the maximum. The results as a function of the input parameters are clustered in order to identify cost-effective combination of drug dose and compound. Therefore, each point in the hidden functions space is labeled to indicate the dose (FIG. 8B) and uptake (FIG. 8C). That dose has a direct effect on the speed of the reaction and the uptake effect shows that the maximum compounding does not necessarily lead to the maximum point in the hidden function space.

Additionally, the points in the hidden space that can be considered as optimal combination treatments, that is those who minimize resources while maximizing output, are identified. To make that determination, the points where both values are above predetermined threshold, for example, 30% of their maximum value are identified. Those points are highlighted in the space plot in FIG. 8D (uptake=150, 73 and dose=1000 (black), uptake=36 and dose=360 (dark gray), uptake=36 and dose=1000 (gray) and uptake=150, 73 and dose=360 (light gray)). The results show that the maximum points over the three hidden functions were achieved by boosting an immense dose while ignoring compounding, which dictates tissue uptake. Nonetheless, the data point achieved by a combination of dose and compounding are positioned in a relatively close vicinity.

Taken together, these results indicate that cost effectiveness of a drug can be increased by compounding lower doses with competent chemicals. As these are merely a fraction of the decision points of possible treatments, it can be done based on specific individual needs. For example, if the subject cannot tolerate high dose or if there is a shortage of the drug in the market, the dose can be reduced and the compounding chemicals that control the uptake increased. Given a specific dose of the drug, the added compounding concentrations may be calculated to decrease the risk of increasing uptake of the drug in tissues prior to the relevant area and consequently reducing the overall impact of the treatment.

Figure 9B:
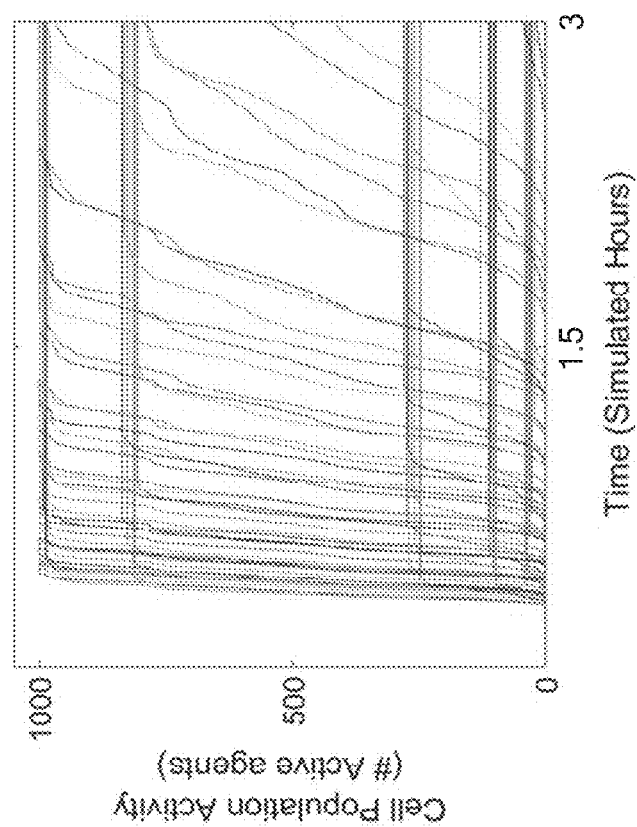
FIG. 9B is a graph showing active cells in the simulation under multiple runs under various initial dose (1000e3:0.1e3 simulated Molar) and tissue uptake (100e-3:0.001e-3 simulated absorption capacity) conditions. Each curve represents a single run of the simulation.
Figure 9A:
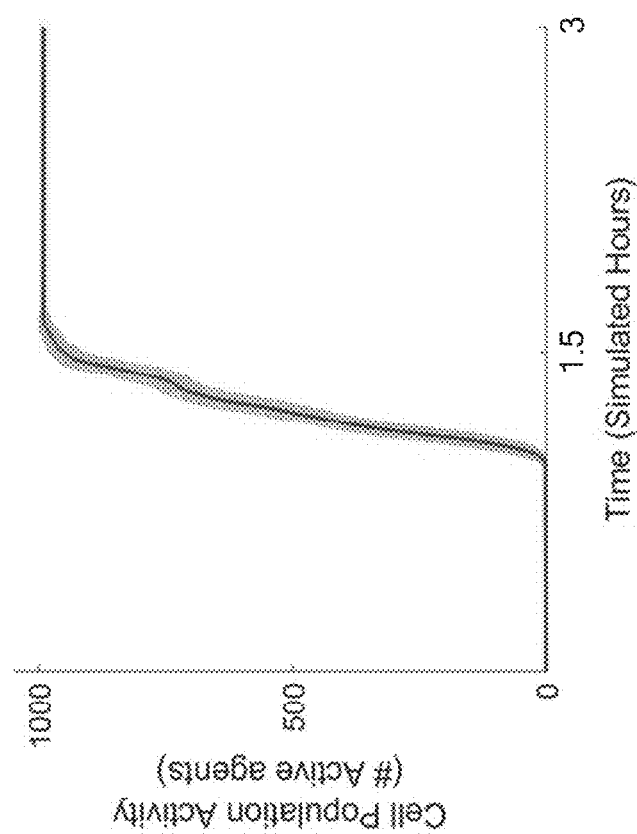
FIG. 9A is a graph showing active cells in the simulation as a function of time under an average of repetitive 10 independent runs of the simulation with dose ~2e3 and uptake ~1e-3. The gray shaded area indicates the error bar over the runs.

Referring now to FIGS. 9A-9B, the activity of the simulated agent population at the simulated substantia nigra area was analyzed over time. FIG. 9A shows an average of 10 independent simulation runs with the standard deviation of the plot (gray shaded area) under a specific dose and a specific tissue uptake (doses ~2e3, uptake ~1e-3). The curve summarizes the number of neurons whose stimulation has been triggered over a simulated period of 3 simulated hours. Three distinct phases in the curve are observed: (1) initial phase of the simulation, where the drug was not yet delivered to the substantia nigra area and thus the total number of stimulated cells equals zero; (2) activity phase, in which drug was taken by the tissue crosses the required threshold and the neuronal population is gradually stimulating its activity; and (3) saturation phase, in which the population reaches equilibrium and maximum number of stimulated cells. This curve can be characterized by three distinct features: (1) the maximum count of simulated agents (i.e., reached its full activity potential) (FIG. 7A), (2) total time of the initial phase until population activity started (FIG. 7D), (3) the slope of population activity as the coefficient of a first order polynomial equation fitted to the curve (FIG. 7G). These features disclose features of each simulation run, namely: (1) maximum capacity, (2) activity lag and (3) reaction rate, respectively.

The simulation was executed over one hundred dose and tissue uptake combinations (in the range of simulated Molar of 1000e3-0.1e3 and simulated absorption units of 100e-3-0.001 e-3, respectively). Each curve in FIG. 9B represents a single run of the simulation under specific dose and tissue uptake combination. The results show that the initial dose and tissue uptake directly dominate the activity of the agent population. Specifically, changes in the three features of each curve are observed. The curves amplitude at the saturation rate varied between the runs, indicating variation in the maximum capacity of the run. Furthermore, the curves shift the activity phase timing, indicting a varying lags in initial stimulation. Finally, the slope of the curve at activity phase is significantly different between the runs, indicating changes in the reaction rate.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of imaging a brain of a living patient, comprising:
   simulating an administration of a drug into brain tissue of a living patient, the simulation including:
      displaying a simulated diffusion of the drug in a three-dimensional virtual reality image of the brain of the living patient;
      displaying simulated brain tissue uptake of the drug in the three-dimensional virtual reality image of the brain of the living patient;
      displaying a simulated stimulation of individual neurons in the three-dimensional virtual reality image of the brain of the living patient; and
      analyzing a simulated activity of the individual neurons based on at least one predetermined property of the drug;
   determining a brain treatment protocol based at least in part on the simulated administration of the drug into the brain of the living patient.

2. The method of claim 1, wherein the three-dimensional virtual reality image of the brain is created and displayed in real-time.

3. The method of claim 1, wherein the simulated administration of the drug into the brain is intranasal.

4. The method of claim 1, wherein the simulated the administration of the drug into brain tissue of the living patient is provided by a virtual reality machine having a virtual reality headset.

5. The method of claim 1, wherein the brain tissue is substantia nigra.

6. The method of claim 1, wherein displaying the simulated diffusion of the drug further includes identifying a nasal passage on the three-dimensional image of the brain and simulating the diffusion of the drug beginning at the image of the nasal passage.

7. The method of claim 1, wherein displaying the simulated diffusion of the drug further includes simulating the diffusion of the drug at a plurality of doses at a plurality of time durations, and displaying the simulated diffusion of the drug at each of the plurality of doses and each of the plurality of time durations.

8. The method of claim 1, wherein displaying the simulated diffusion of the drug includes:
   assigning a plurality of voxels to the brain tissue in the three-dimensional virtual reality image of the brain of the living patient;
   determining a diffusion coefficient between adjacent ones of the plurality of voxels based in part on an MRI intensity in each of the plurality of voxels;
   determining a concentration of the drug in each of the plurality of voxels based in part on the diffusion coefficient between adjacent ones of the plurality of voxels; and
   displaying the simulated diffusion of the drug in real time.

9. The method of claim 1, wherein displaying the simulated brain tissue uptake of the drug includes:
   assigning a plurality of voxels to the brain tissue in the three-dimensional virtual reality image of the brain of the living patient;
   determining an absorption coefficient for each of plurality of voxels based in part on an MRI intensity in each of the plurality of voxels;
   determining a tissue uptake of the drug in each of the plurality of voxels based in part on the absorption coefficient in each of the plurality of voxels; and
   displaying the simulated brain tissue uptake of the drug in real time.

10. The method of claim 1, displaying a simulated stimulation of individual neurons includes:
   assigning a plurality of voxels to the brain tissue in the three-dimensional virtual reality image of the brain of the living patient, each voxel being associated with at least one individual neuron;
   uniformly assigning a plurality of simulated reactive agents within an area of the image occupied by the substantia nigra in the three-dimensional virtual reality image of the brain of the living patient, each of the plurality of simulated reactive agents being configured to respond to a predetermined environmental condition; and
   if one of the plurality of simulated reactive agents responds to the predetermined environmental condition, providing a visual indication of the response in an associated one of the plurality of voxels in real time.

11. The method of claim 1, wherein analyzing a simulated activity of the individual neurons based on at least one predetermined property of the drug includes characterizing the simulated activity of the individual neurons at a predetermined dose of the drug as at least one from the group consisting of:
 a. unstimulated;
 b. stimulated and partially activated; and
 c. stimulated and fully activated.

12. The method of claim 1, wherein determining a brain treatment protocol based at least in part on the simulated administration of the drug into the brain of the living patient includes determining an initial dosing of the drug.

13. A system for imaging the brain, comprising:
 a control unit having a processor, the processor having processing circuitry configured to:
 simulate an administration of a drug into brain tissue of the living patient, the processing circuitry being further configured to:
  display a simulated diffusion of the drug in a three-dimensional virtual reality image of the brain of the living patient;
  display simulated brain tissue uptake of the drug in the three-dimensional virtual reality image of the brain of the living patient;
  display a simulated stimulation of individual neurons in the three-dimensional virtual reality image of the brain of the living patient; and
  analyze a simulated activity of the individual neurons based on at least one predetermined property of the drug; and
 determine a brain treatment protocol based at least in part on the simulated administration of the drug into the brain of the living patient.

14. The system of claim 13, wherein displaying the simulated diffusion of the drug further includes simulating the diffusion of the drug at a plurality of doses at a plurality of time durations, and displaying the simulated diffusion of the drug at each of the plurality of doses and each of the plurality of time durations.

15. The system of claim 13, wherein displaying the simulated diffusion of the drug includes:
 assigning a plurality of voxels to the brain tissue in the three-dimensional virtual reality image of the brain of the living patient;
 determining a diffusion coefficient between adjacent ones of the plurality of voxels based in part on an MRI intensity in each of the plurality of voxels;
 determining a concentration of the drug in each of the plurality of voxels based in part on the diffusion coefficient between adjacent ones of the plurality of voxels; and
 displaying the simulated diffusion of the drug in real time.

16. The system of claim 13, wherein displaying simulated brain tissue uptake of the drug includes:
 assigning a plurality of voxels to the brain tissue in the three-dimensional virtual reality image of the brain of the living patient;
 determining an absorption coefficient for each of plurality of voxels based in part on an MRI intensity in each of the plurality of voxels;
 determining a tissue uptake of the drug in each of the plurality of voxels based in part on the absorption coefficient in each of the plurality of voxels; and
 displaying the simulated brain tissue uptake of the drug in real time.

17. The system of claim 13, displaying a simulated stimulation of individual neurons includes:
 assigning a plurality of voxels to the brain tissue in the three-dimensional virtual reality image of the brain of the living patient, each voxel being associated with at least one individual neuron;
 uniformly assigning a plurality of simulated reactive agents within an area of the image occupied by the substantia nigra in the three-dimensional virtual reality image of the brain of the living patient, each of the plurality of simulated reactive agents being configured to respond to a predetermined environmental condition; and
 if one of the plurality of simulated reactive agents responds to the predetermined environmental condition, providing a visual indication of the response in an associated one of the plurality of voxels in real time.

18. The system of claim 13, wherein analyzing a simulated activity of the individual neurons based on at least one predetermined property of the drug includes characterizing the simulated activity of the individual neurons at a predetermined dose of the drug as at least one from the group consisting of:
 a. unstimulated;
 b. stimulated and partially activated; and
 c. stimulated and fully activated.

19. The system of claim 13, wherein the processing circuitry is configured to create and display in real-time.

20. A method of imaging a brain of a living patient, comprising:
 capturing a plurality of three-dimensional images of the brain of the living patient with magnetic resonance imaging (MRI);
 simulating an intranasal administration of a drug into brain tissue of the living patient in real-time, the simulation including:
  displaying a simulated diffusion of the drug in a three-dimensional virtual reality image of the brain of the living patient;
  displaying simulated brain tissue uptake of the drug in the three-dimensional virtual reality image of the brain of the living patient;
  displaying a simulated stimulation of individual neurons in the substantia nigra three-dimensional virtual reality image of the brain of the living patient; and
  analyzing a simulated activity of the individual neurons based on at least one predetermined property of the drug;
 determining a drug dosing based at least in part on the simulated administration of the drug into the brain of the living patient.

* * * * *